United States Patent [19]
Cansell et al.

[11] Patent Number: 5,691,641
[45] Date of Patent: Nov. 25, 1997

[54] NMR PICKUP DEVICE DELIVERING A SIGNAL REPRESENTATIVE OF BREATHING OF A PATIENT

[75] Inventors: Albert Cansell, Wissembourg; Michel Kraemer, Durrenbach; Christian Brevard, Wissembourg, all of France; Jacques Felblinger, Bern; Chris Boesch, Thun, both of Switzerland

[73] Assignee: "O.D.A.M." Office de Distribution d'Appareils Medicaux (Societe Anonyme), Wissembourg, France

[21] Appl. No.: 585,018

[22] Filed: Jan. 11, 1996

[30] Foreign Application Priority Data

Jan. 9, 1995 [FR] France ................... 95 00335

[51] Int. Cl.⁶ ............... G01R 33/34; A61B 5/055
[52] U.S. Cl. ...................... 324/309; 128/653.2
[58] Field of Search ...................... 324/307, 309, 324/318, 300, 314, 322; 128/653.2, 653.5, 653.3

[56] References Cited

U.S. PATENT DOCUMENTS

| | | | |
|---|---|---|---|
| 4,751,462 | 6/1988 | Glover et al. | 324/309 |
| 5,038,785 | 8/1991 | Blakeley et al. | 128/653.2 |
| 5,209,233 | 5/1993 | Holland et al. | 128/653.2 |

FOREIGN PATENT DOCUMENTS

| | | |
|---|---|---|
| 0 498 996 | 8/1992 | European Pat. Off. |
| WO 87/00922 | 2/1987 | WIPO |
| WO 94/23648 | 10/1994 | WIPO |

Primary Examiner—Sandra L. O'Shea
Assistant Examiner—Roger Phillips
Attorney, Agent, or Firm—Young & Thompson

[57] ABSTRACT

A detector device delivering a signal representative of the respiration of a patient, adapted to be used in a charged and sensitive electromagnetic environment. The device is principally constituted by at least two non-metallic electrodes (1) and by a unit for the processing of electrical signals emitted by the heart, comprising a first module (5) for acquiring and shaping cardiac electric signals, a second module (6) for extraction of the respiratory signal, and a third module (7) for electro-optical conversion of this latter, the modules being disposed in a shielded casing (8) forming a Faraday cage and, finally, by an optical connection (9) connecting the casing (8) to at least one other apparatus or device.

21 Claims, 4 Drawing Sheets

NMR PICKUP DEVICE DELIVERING A SIGNAL REPRESENTATIVE OF BREATHING OF A PATIENT

FIELD OF THE INVENTION

The present invention relates to the field of picking up and measuring biological signals and the surveillance of patients, particularly of patients under NMR (Nuclear Magnetic Resonance) examination for example in a magnetic resonance imager (MRI), and has for its object a pickup device delivering particularly a signal representative of the breathing of a patient.

BACKGROUND OF THE INVENTION

At present, the respiratory movements and/or the respiratory flow of a patient are principally picked up by means either of specific electronic detectors, measuring the air flow or temperature at the level of the nostrils, or by dedicated devices registering the deformations of the thorax by means of a transducer associated with a mechanical, hydraulic or pneumatic detector and delivering an electrical signal as a function of said deformations.

However, in an MRI environment, the known devices do not permit picking up in a precise, reliable and reproducible manner the respiratory rhythm because particularly of the nature itself of the physical magnitudes measured, the electromagnetic disturbances and the modes of acquisition and measurement used, and of the primary importance of the positioning of the detectors, which are often difficult to install correctly and frequently involuntarily displaced in the course of the measuring cycle by the patient.

More particularly, the production of electrical signals in a charged and sensitive electromagnetic environment, such as that of an NMR apparatus, gives rise to a harmful disturbance of said environment and, conversely, a disturbance of the electrical measurement signals produced, falsifying their meaning.

Moreover, the cables and other electrical conductors, forming antennae, disturb the electromagnetic environment of the NMR apparatus and falsify the measurements and, in the case of an imager, the virtual reconstruction (images) obtained by this latter, even when said cables are sheathed and twisted.

Conversely, field gradients, the radiofrequency fields and the phenomena connected with the commutations between emitting and receiving windings in the course of a test of the NMR type, strongly disturb the transmission of the picked up signals and can, by generation of important artificial signals, render these latter totally useless, the patient being disposed within the interior itself of the principal magnet of the NMR apparatus.

Moreover, possible movements of the patient (particularly respiration itself) give rise to movements of said electrical transmission cables in the ambient field, from which automatically results an induction of potential generators of false signals.

Moreover, the harmful phenomena recited above are strongly amplified when the transmission cables have one or several loops.

Furthermore, the solution consisting in gaining and transmitting information or signals in pneumatic or hydraulic form outside the sensitive electromagnetic environment is no longer satisfactory because of the lack of reliability and precision of these modes of transmission and the important losses which they involve, of the problems of positioning the detector and of the inconvenience to the patient.

Moreover, pneumatic or mechanical detectors are all subject to strong shunting which it is necessary continuously to compensate.

Still further, the pneumatic or mechanical detectors react only to a given type of respiration, namely, thoracic or diaphragmatic, and are semi-insensitive as to the other type, this as a function of the positioning of said detectors on the patient.

However, in certain patients only one of the two types of mentioned respiration is substantially predominant, the other type being of insufficient or even negligible amplitude.

SUMMARY OF THE INVENTION

The problem to be solved by the present invention consists accordingly in conceiving a less cumbersome detector device, picking up in a precise and reliable manner the respiratory signal or the signal corresponding to the respiratory movements of a patient and converting it to a form transmissible without disturbance in a charged electromagnetic environment, said detector device being able to be used with complete safety and without reciprocal influence on the patient disposed in the NMR apparatus.

Moreover, said detector device should also, according to a second object of the invention, be able to pick up and transmit independently of other physiological signals or other control apparatus, without substantially increasing its size or the complexity of its construction.

Furthermore, the detector device should not have drift, or only a drift of small amplitude and which is controllable, and should be able to pick up signals generated by diaphragmatic breathing, as well as those generated by thoracic breathing.

To this end, the present invention has for its object a detector device delivering particularly a signal representative of the breathing of a patient, adapted to be used in a charged and sensitive electromagnetic environment, particularly adjacent or within a nuclear magnetic resonance apparatus, and more particularly on a patient within the tunnel of the magnet of an MRI, characterized that it is principally constituted, on the one hand, by at least two non-metallic electrodes, mounted on a base of a support body of a non-magnetic material and adapted to be applied against the skin of a patient in the cardiac region, on the other hand, by a process unit for the electrical signals emitted by the heart, comprising a first acquisition and shaping module for the cardiac electric signals, a second module for the extraction of the respiratory signal and a third module for electrooptic conversion of this latter, disposed in a shielded casing forming a Faraday cage and carried by the base and, finally, by optical connection means connecting said casing to at least one other apparatus or device located as the case may be within the charged and sensitive electromagnetic environment.

BRIEF DESCRIPTION OF THE DRAWINGS

The invention will be better understood from the following description, which relates to a preferred embodiment, given by way of non-limiting example, and explained with reference to the accompanying schematic drawings, in which.

DESCRIPTION OF THE PREFERRED EMBODIMENTS

Figure 1:
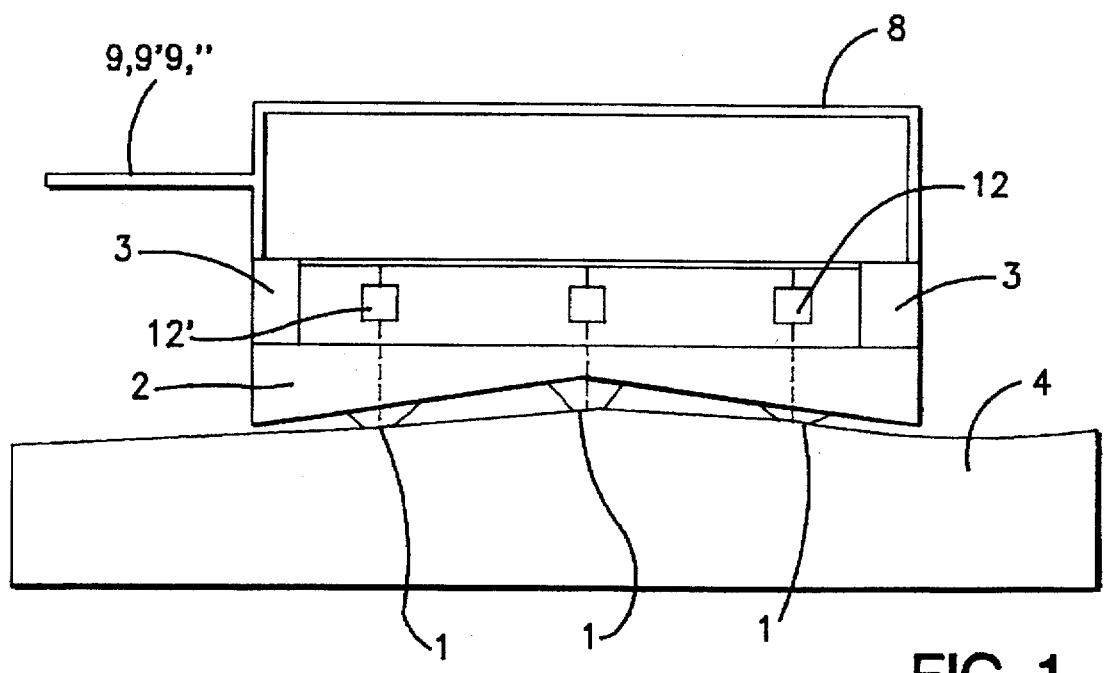
FIG. 1 is an external schematic view, in side elevation, of the detector device according to the invention.
Figure 3:
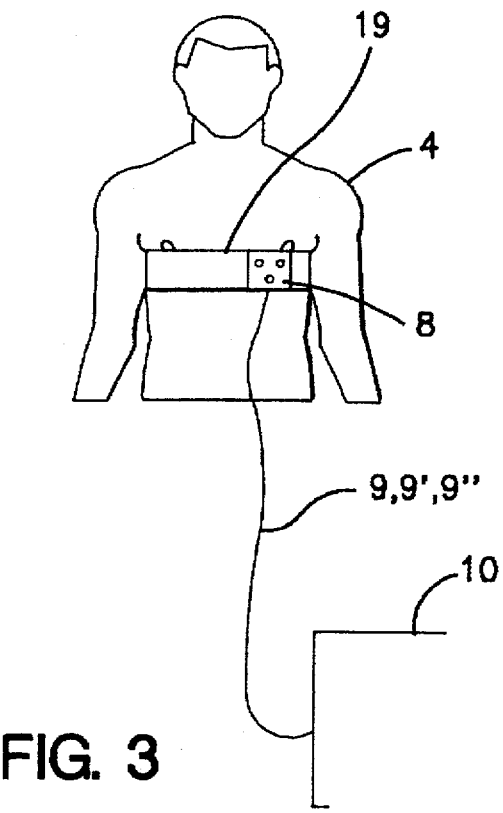
FIG. 3 is a schematic view showing the use of the detector device shown in FIG. 1.
Figure 2:
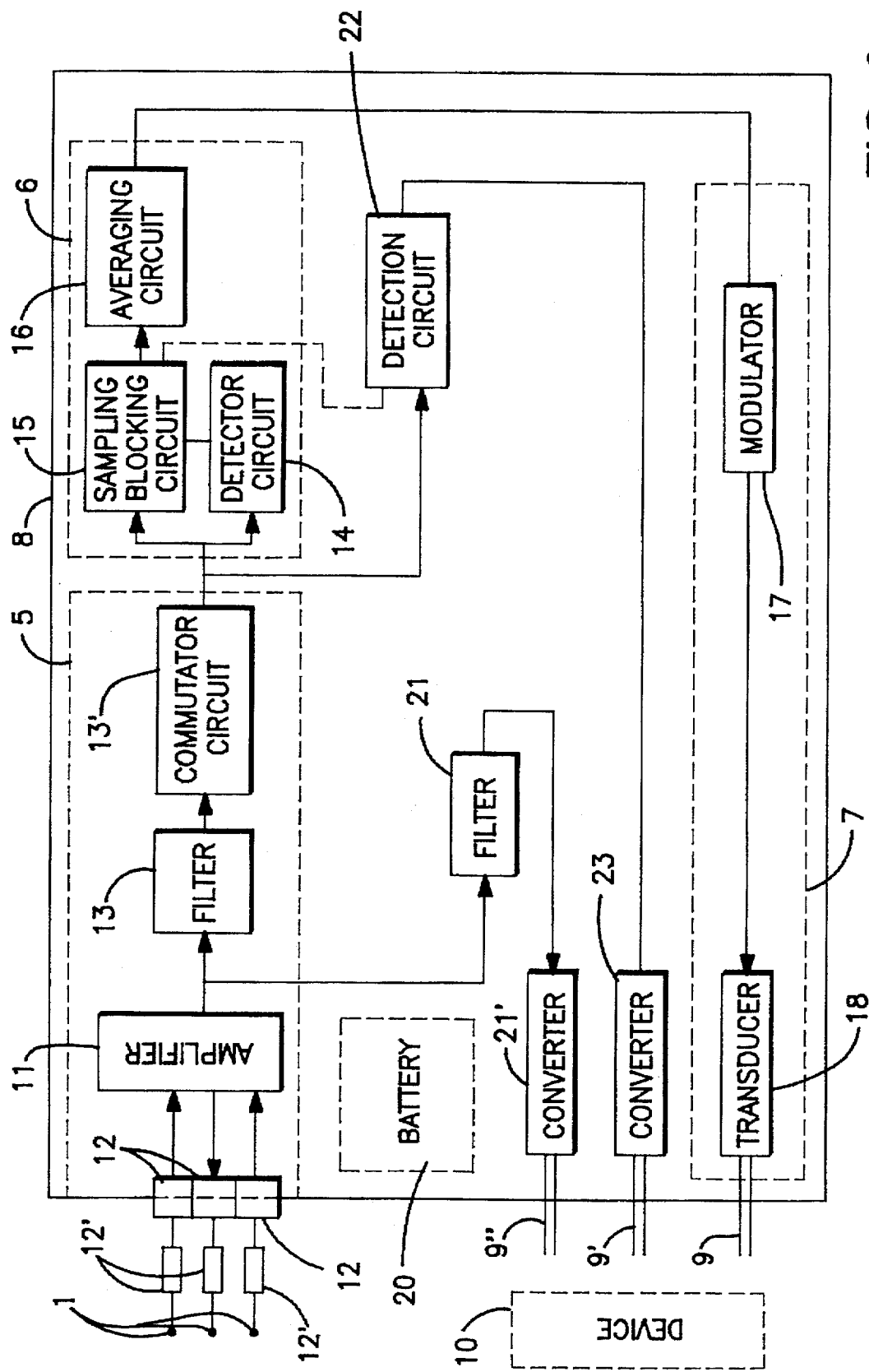
FIG. 2 is an operating diagram of the detector device shown in FIG. 1.

According to the invention, and as shown in FIGS. 1, 2 and 3 of the accompanying drawings, the detector device is principally constituted, on the one hand, by at least two non-metallic electrodes 1, mounted on a base 2 of a support body 3 of a non-magnetic material and adapted to be applied against the skin of the patient 4 in the cardiac region, on the other hand, by a processing unit for the electric signals emitted by the heart, comprising a first acquisition and shaping module 5 for the electric cardiac signals, a second module 6 for the extraction of the respiratory signal and a third module 7 for electro-optical conversion of this latter, disposed in a shielded casing 8 forming a Faraday cage and carried by the base 2, and, finally, by optical connection means 9 connecting said casing 8 to at least one other apparatus or device 10 located as the case may be outside the charged and sensitive electromagnetic environment.

The present invention is accordingly based on the extraction of the respiratory signal from the electrocardiograph signals picked up in a very precise way by the electrodes 1 and immediately processed after their pickup, without transmission, in a suitable unit totally insulated from the external electromagnetic environment.

Figure 4:
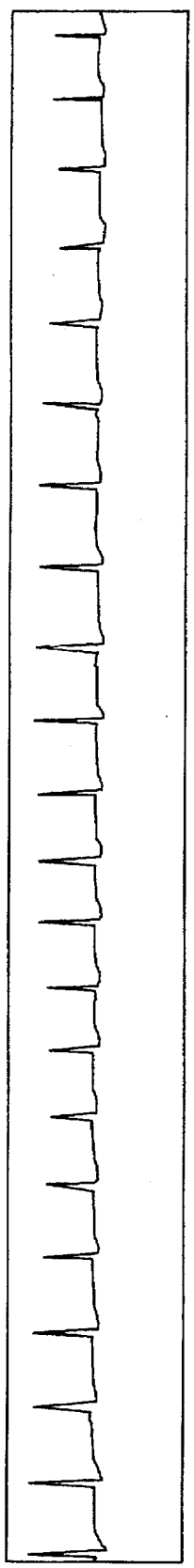
FIG. 4 represents an available electrocardiogram signal, after suitable filtering, at the outlet of the acquisition stage of the first module of the treatment unit forming a portion of the detector device shown in FIG. 2.

To this end, as shown particularly in FIG. 4 of the accompanying drawings, the electrocardiogram signal, constructed from electrical signals emitted by the heart and comprised by a sequence of QRS complexes, is subjected to periodical amplitude variation whose phase and period correspond to the respiratory cycle.

This phenomenon is explained by the fact that, in the course of the respiratory cycle of the patient, the heart is displaced periodically by the successive movements of expansion and contraction of the thoracic cage and the resulting movements of the other organs which are disposed within it, which gives rise directly to a displacement of the electrical axis of the heart.

It is therefore this direct checking of the cyclic respiratory movements by the electrocardiogram signal which is used to the profit of the invention to extract from this latter the respiratory signal.

According to a first characteristic of the invention, the first module 5 comprises on the one hand an acquisition stage of the electrocardiac signals picked up by the electrodes 1, constituted essentially by an instrumentation amplifier 11 each of whose inlets is connected to a corresponding electrode 1 by means of a radiofrequency filter 12 and a limit resistance 12', and, on the other hand, a shaping stage comprised by a pass band filter 13 and a commutator circuit 13'.

The filters 12 and the resistances 12', disposed between the instrumentation amplifier 11 and the electrodes 1, serve respectively to eliminate parasites induced by the environmental radiofrequency emissions and to reduce the possible currents induced by these latter, the connections between the electrodes 1 and the casing 8 being moreover provided by rigid wires.

Preferably, said electrodes 1 are three in number and are of a conductive material selected from the group comprised by carbon, carbon compounds and loaded plastic materials, one of said electrodes 1 being used to increase the rejection size of the common mode.

Moreover, the electrodes 1 being secured to the base 2, the relative positions of them to each other are fixed, by being spaced a distance which can be a function of the size of the patient and it suffices to position said base 2 adjacent the heart so that the electrodes 1 will be placed in a satisfactory manner.

The only external metallic element of the detector device, namely the shielded casing 8, will as a result never be in direct contact with the patient 4, because it will be at least separated from this latter by said base 2, which avoids any risk of burning.

Figure 6:
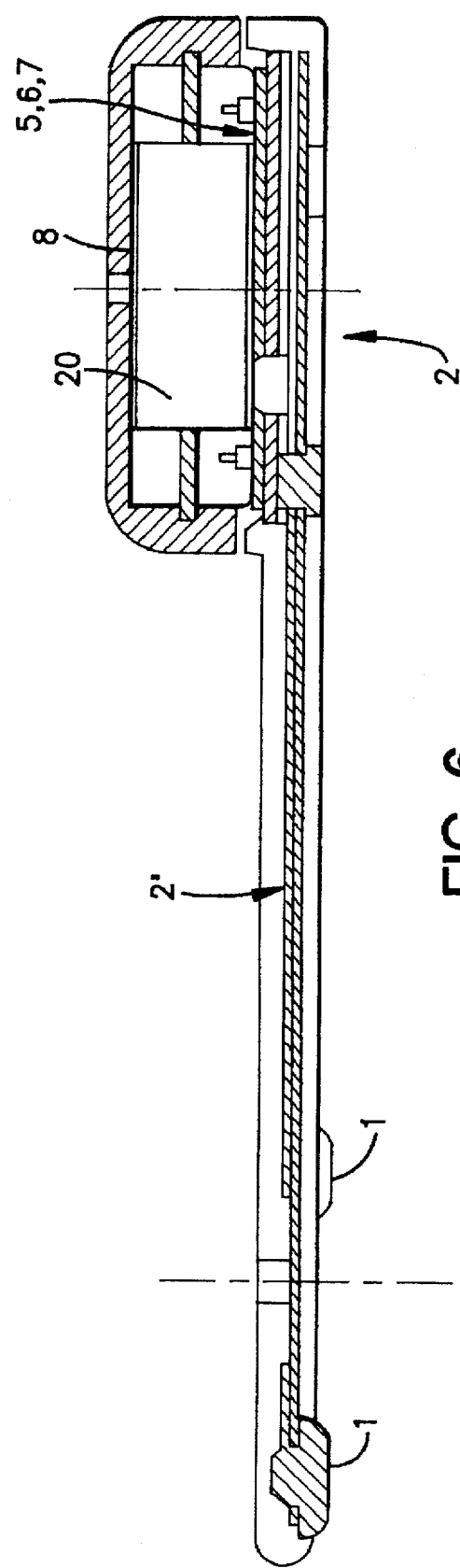
FIG. 6 is a side elevational and cross-sectional view of a second embodiment of the detector shown in FIG. 1.

According to a second embodiment of the detector device according to the invention, shown in FIG. 6 of the accompanying drawings, the electrodes 1 are not positioned below the casing 8, but are spaced from this latter and secured to the end of a lateral prolongation 2', of small thickness, of the base 2, the connection between said electrodes 1 and the casing 8 being effected by non-metallic conductors, for example of carbon fibers.

Such a construction of the detector device permits spacing the casing 8, which has a substantial height or thickness, from the reception points of the EKG in the cardiac region, where it may be necessary, as the case may be, to apply an MRI measuring antenna as close as possible to the skin of the patient.

Preferably, the pass-band filter 13 of the first module 5 permits ridding the signal delivered by the instrumentation amplifier 11 of its superfluous and useless components for the ultimate treatment and to isolate the portions of the signals (the successive QRS complexes) whose variation of amplitude with respiration is to be measured.

This pass-band filter 13 can for example be constituted by the combination of a low-pass filter and a high-pass filter, together delimiting a pass-band of about 15 Hz to 35 Hz.

Furthermore, the redresser circuit 13' permits obtaining at the outlet of said module 5 a signal which is always polarized in a known and predetermined direction. Thus, as a function of the position of the electrodes 1 relative to the body, the electrocardiogram signal delivered by the instrumentation amplifier 11 can be polarized different and oppositely.

As shown in FIG. 2 of the accompanying drawings, the second module 6 preferably comprises a maxima detector circuit 14, supplied by the shaped signal from the first module 5 and controlling a sampling-blocking circuit 15 also supplied by the signal from said first module 5, the output signal of said sampling-blocking circuit 15 being processed by an averaging and smoothing circuit 16.

Thus, the detector circuit 14 permits detecting the times of appearance of the signal shaped or controlled by the first stage of the first module 5, signals of which it is desired to measure the amplitude of a predetermined point, for example the maximum amplitude.

This detection is used to control the sampling-blocking circuit 15 which carries out the measurement and ensures the maintenance of the picked up amplitudes which vary with the successive QRS complexes as a function of the respiratory cycles. The signal from said circuit 15 is in the form of a series of shoulders of amplitudes variable with the respiration and representing schematically the respiratory signal.

This structure permits preventing the signal from the circuit 15 from being affected by false voltage signals which can exist in the signal from the instrumentation amplifier 11 between two successive measurements of amplitudes and which have no relation to the cardiac activity and whose amplitude is in no case connected to the respiratory activity.

The circuit 16 calculates the mean value of the signal from the sampler-blocker 15 and suppresses in it the component of continuous voltage, the signal delivered by this circuit representing as a result precisely the respiratory signal.

As a modification, the second module 6 can have the form of a digital integrated circuit or of several programmable digital integrated circuits permitting the numerical processing of the signals delivered by the first module 5 and supplying a signal representative of the breathing or a synchronization signal derived from the respiratory signal to the third module 7.

According to another characteristic of the invention, shown also in FIG. 2 of the accompanying drawings, the third module 7 is preferably comprised by a modulator circuit 17, for example for a frequency modulation or pulse width, receiving the signal delivered by the second module 6 and of an electro-optical transducer 18 connected to an optical conductor 9 constituting the optical connection means.

This latter can deliver the respiratory signal, for example, to a display and recordation device, to a control means for the NMR apparatus or of a supplemental device, or to several of these apparatus, devices or the like after derivation or multiplexing of said optical conductor.

According to a preferred embodiment of the invention shown in FIG. 3 of the accompanying drawings and so as to ensure a firm positioning of the electrodes 1 and to guarantee pickup of cardiac electrical signals as close as possible to the heart, there is provided a belt 19 or a harness of a non-metallic material, if desired elastic, provided with quick closure means and length adjustment means and traversing the support body 3 or at least one handle secured to said support body 3, said belt 19 or harness ensuring the positioning in translation and in rotation of said support body 3 and of said electrodes 1.

Thus, the base 2 of the support body 3 and hence the electrodes 1 will be permanently applied forcibly against the skin of the patient adjacent the heart.

According to a first modified embodiment of the invention, the shielded casing 4 contains also a battery 20 or a long-life rechargeable accumulator of the amagnetic type, an optical conductor, associated with an optical control switch disposed in the casing 8, which can permit controlling the operation and the supply of said processing unit 5, 6, 7 and as the case may be the adjustment of the different circuits comprising its constituent modules (not shown).

According to a second modified embodiment of the invention, the energy supply of the processing unit is constituted by means of an optical conductor coacting with a photovoltaic cell or like device disposed in the casing.

According to a supplemental characteristic of the invention, shown in FIG. 2 of the accompanying drawings, the detector device can also comprise an independent supplemental unit for processing signals delivered by the acquisition stage of the first module 5, comprised essentially of a low-pass filter 21, having a cut-off frequency at around 20 Hz, and a module 21' for electro-optic conversion, connected to a second optical connection means 9'.

Such a supplemental processing unit is particularly described in French patent application No. 2 704 131 in the name of the applicant.

Thus, thanks to this latter arrangement, it is possible to deliver independently two important physiological signals of different natures, elaborated from the same electrocardiac starting signals, by separate processing and particularly filtering adapted to each of the processing paths, carried out in immediate proximity to the place where the starting signals were picked up, According to another supplemental characteristic of the invention, the detector device can comprise moreover a circuit 22 for cyclic detection of a particular point or level of the repeating signal (electrocardiogram modulated in amplitude by respiration) delivered by the first module 5 and to provide a synchronization signal at each occurrence and detection of said predetermined point or level, said detection circuit 22 being followed by a corresponding electro-optical converter 23 connected to an optical connection means proper 9".

As a modification, said detection circuit 22 could also be supplied by a signal from the sampling-blocking circuit 15 forming a part of the second module 6.

The synchronization signals delivered by the detection circuit 22 will correspond to the approximate success of coincidences, repeated periodically, between a given point of a QRS complex (for example its maximum) of the electrocardiogram signal, and a given point of the respiratory signal.

This signal, which constitutes a timed marker, accordingly permits determining timewise and to repeat in a repetitive manner a given condition of the heart in a given position of this latter, in the course of a respiratory cycle.

Figure 5:
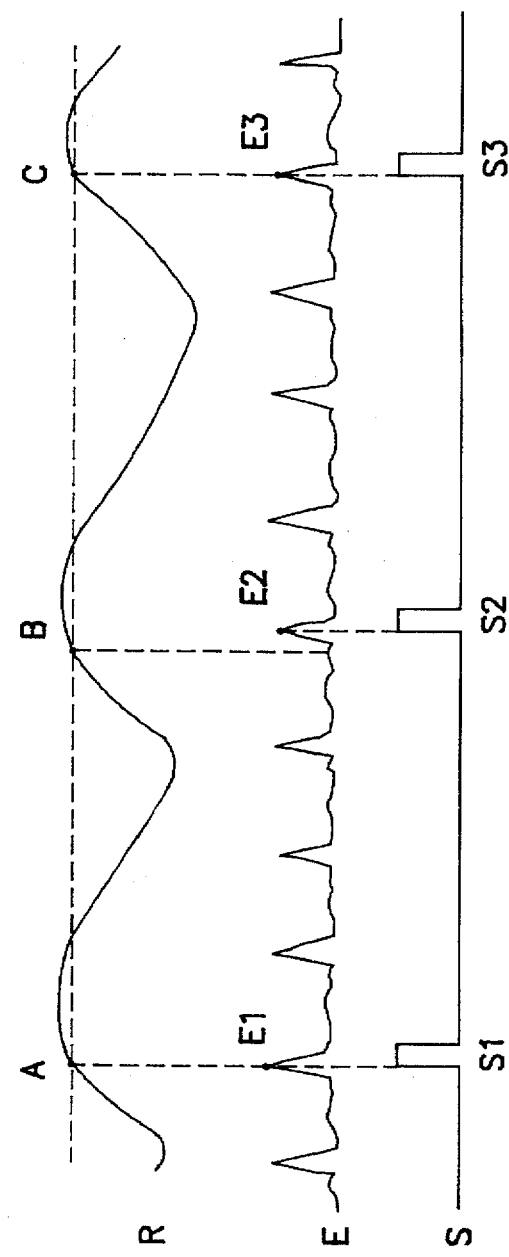
FIG. 5 shows schematically and simultaneously the curves of the respiratory signal R, of the electrocardiogram signal E and of the synchronization signal S delivered by the cyclic detection circuit according to the invention.

The manner of operation of the circuit 22 and the meaning of the signal supplied by this latter, can be explained more precisely with reference to FIG. 5 of the accompanying drawings.

Taking as a reference the respiratory signal, a time location A can be defined, coinciding with a QRS complex E1 and there can be sought during the period following the respiratory signal, at the same position in the cycle B, the QRS complex E2 which is the closest, and so on for the following cycles (cycle C and QRS E3, etc.).

From the QRS's E1, E2, E3, etc., can be derived the synchronization pulses of the image (also known as "TRIGGER signal") such as S1, S2, S3, etc., taking directly into account the two cardiac and respiratory activities.

The NMR images can also be produced with constant offsets of time relative to the time references corresponding to the pulses S1, S2, S3, etc.

Such a synchronization signal, indicating the successive occurrences of a predetermined point or level in the respiratory signal, is thus particularly interesting in the framework of NMR imagery to trigger repetitive sequences of taking of images, forming by superpositions and virtual reconstruction of the final image.

As a modification of the use of EKG signals and of respiratory movements such as described above in the case of production of an NMR image, there can be provided NMR images at each occurrence of a complex QRS and by using each of these latter as image synchronization pulses, the respiratory signal being picked up and registered simultaneously and separately by the detector device.

Then, during ultimate use of the produced NMR images, the respiratory signal is used to extract and select the NMR images which correspond to a predetermined and repetitive point on the respiratory cycle (respiratory compensation).

Thus, the detector device according to the invention permits synchronizing the taking of NMR images and/or the formation of NMR images on the basis of two physiologic signals, namely the EKG signal and the respiratory signal, and hence to take account of the two types of physiologic movements for the formation of said images.

Of course, the invention is not limited to the embodiment described and shown in the accompanying drawings. Modifications remain possible, particularly as to the construction of the various elements or by substitution of technical equivalents, without thereby departing from the scope of protection of the invention.

We claim:

1. In a detector device for delivering a signal representative of the respiration of a patient, adapted to be used in a charged and sensitive electromagnetic environment, adjacent or within a nuclear magnetic resonance apparatus, and by a patient within the tunnel of the magnet of an MRI, the improvement wherein the device comprises: at least two non-metallic electrodes mounted on a base of a support body of a non-magnetic material and adapted to be applied against the skin of the patient in the cardiac region; a processing unit for processing electrical signals emitted by the heart, comprising a first module for acquiring and shaping cardiac electric signals, a second module for extracting the respiratory signal, and a third module for electro-optical conversion of the respiratory signal, said processing unit being disposed in a shielded casing forming a Faraday cage and carried by the base; and an optical connection means connecting said casing to at least one other apparatus located outside the charged and sensitive electromagnetic environment.

2. Detector device according to claim 1, wherein the first module comprises an acquisition stage for the electrocardiac signals picked up by the electrodes, consisting essentially of an instrumentation amplifier of which each of the inputs is connected to a corresponding electrode by means of a radiofrequency filter and by a limit resistance, and a stage for placing in composed shape a passband filter and a commutation circuit.

3. Detector device according to claim 1, wherein the second module comprises a maxima detector circuit supplied by the shaped signal from the first module and controlling a sampling-blocking circuit also supplied by the shaped signal from said first module, the output signal of said sampling-blocking circuit being processed by an averaging and smoothing circuit.

4. Detector device according to claim 1, wherein the third module comprises a modulator circuit for frequency modulation or pulse width modulation, receiving the signal delivered by the second module and by an electro-optic transducer connected to an optical conductor constituting the optical connection means.

5. Detector device according to claim 1, wherein the electrodes are three in number and are of a conductive material selected from the group consisting of carbon, carbon compounds and loaded plastic materials, one of said electrodes being used to increase the rejection size in a common mode.

6. Detector device according to claim 1, further comprising a harness of a non-magnetic material, provided with quick closure means and length adjustment means and passing through one of the support body and a handle secured to the support body, said harness ensuring the positioning in translation and in rotation of said support body and of said electrodes.

7. Detector device according to claim 1, wherein the shielded casing further comprises one of a battery and a long-life rechargeable accumulator which is of non-magnetic type, an optical conductor associated with an optical control switch disposed in the casing for controlling the operation and the supply of said processing unit and the adjustment of the different circuits comprising its constituent modules.

8. Detector device according to claim 1, wherein the processing unit is supplied with energy by means of an optical conductor coacting with a photovoltaic cell disposed in the casing.

9. Detector device according to claim 2, further comprising a supplemental independent unit for processing signals delivered by the acquisition stage of the first module, said supplemental independent unit including a low-pass filter having a cut-off frequency of about 20 Hz, and an electro-optical conversion module connected to a second optical connection means.

10. Detector device according to claim 2, further comprising a detection circuit for cyclic detection of a predetermined point or level of a repeating signal delivered by the acquisition stage of the first module and for supplying a synchronization signal at each occurrence and detection of said predetermined point or level, said detection circuit being followed by a corresponding electro-optical converter connected to an optical connection means proper.

11. Detector device according to claim 10, wherein the detection circuit is supplied by the signal from the sampling-blocking circuit forming a part of the second module.

12. Detector device according to claim 10, further comprising means for using the synchronization signal indicating the successive occurrences of a predetermined point or level in the respiratory signal to trigger the repetitive sequences of NMR image taking, forming by superposition and virtual reconstruction a final image.

13. Detector device according to claim 1, wherein the electrodes are remote from the shielded casing and are fixed on the end of a lateral prolongation of small thickness, of the base, the connection between said electrodes and the casing being effected by non-metallic conductors.

14. In a detector device for delivering a signal representative of the respiration of a patient, adapted to be used in a charged and sensitive electromagnetic environment, adjacent or within a nuclear magnetic resonance apparatus, and by a patient within the tunnel of the magnet of an MRI, the improvement wherein the device comprises at least two non-metallic electrodes connected to a support body of a non-magnetic material and adapted to be applied against the skin of the patient in the cardiac region; a processing unit for processing electrical signals emitted by the heart, comprising a first module for acquiring and shaping cardiac electric signals, a second module for extracting the respiratory signal, and a third module for electro-optical conversion of the respiratory signal, said processing unit being disposed in a shielded casing forming a Faraday cage and carried by the support body; and an optical connection means connecting said casing to at least one other apparatus located outside the charged and sensitive electromagnetic environment.

15. Detector device according to claim 14, wherein the first module comprises an acquisition stage for the electrocardiac signals picked up by the electrodes, consisting essentially of an instrumentation amplifier of which each of the inputs is connected to a corresponding electrode by means of a radiofrequency filter and by a limit resistance, and a stage for placing in composed shape a passband filter and a commutation circuit.

16. Detector device according to claim 14, wherein the second module comprises a maxima detector circuit supplied by the shaped signal from the first module and controlling a sampling-blocking circuit also supplied by the shaped signal from said first module, the output signal of said sampling-blocking circuit being processed by an averaging and smoothing circuit.

17. Detector device according to claim 14, wherein the third module comprises a modulator circuit for frequency modulation or pulse width modulation, receiving the signal delivered by the second module and by an electro-optic transducer connected to an optical conductor constituting the optical connection means.

18. Detector device according to claim 15, further comprising a supplemental independent unit for processing signals delivered by the acquisition stage of the first module, said supplemental independent unit including a low-pass filter having a cut-off frequency of about 20 Hz, and an electro-optical conversion module connected to a second optical connection means.

19. Detector device according to claim 15, further comprising a detection circuit for cyclic detection of a predetermined point or level of a repeating signal delivered by the acquisition stage of the first module and for supplying a synchronization signal at each occurrence and detecting of said predetermined point or level, said detection circuit being followed by a corresponding electro-optical converter connected to an optical connection means proper.

20. Detector device according to claim 19, wherein the detection circuit is supplied by the signal from the sampling-blocking circuit forming a part of the second module.

21. Detector device according to claim 19, further comprising means for using the synchronization signal indicating the successive occurrences of a predetermined point or level in the respiratory signal to trigger the repetitive sequences of NMR image taking, forming by superposition and virtual reconstruction a final image.

* * * * *